United States Patent [19]

Andersson et al.

[11] 4,305,295

[45] Dec. 15, 1981

[54] PORTABLE APPARATUS FOR MEASURING ACOUSTIC IMPEDANCE AT THE SURFACE OF CURVED SOUND ABSORBER

[75] Inventors: Anders O. Andersson, Seattle; Robert B. Purves, Kent, both of Wash.

[73] Assignee: The Boeing Company, Seattle, Wash.

[21] Appl. No.: 106,992

[22] Filed: Dec. 26, 1979

[51] Int. Cl.³ .......................................... G01N 29/00
[52] U.S. Cl. ...................................... 73/589; 73/584
[58] Field of Search ............... 73/589, 584, 583, 579, 73/574; 181/286

[56] References Cited

U.S. PATENT DOCUMENTS

| | | | |
|---|---|---|---|
| 2,981,096 | 4/1961 | Carrell | 73/589 |
| 3,068,370 | 12/1962 | McInnish | 73/628 |
| 3,960,004 | 6/1976 | Wirt et al. | 73/589 |
| 3,996,788 | 12/1976 | Purves | 73/38 |
| 4,144,768 | 3/1979 | Andersson et al. | 73/646 |

*Primary Examiner*—Stephen A. Kreitman
*Attorney, Agent, or Firm*—Conrad O. Gardner; B. A. Donahue

[57] ABSTRACT

The apparatus consists of a circular, flexible disc held at a constant distance from a curved absorbing surface by pins or flexible ribs. Sound from a loudspeaker is fed to the center of the disc and allowed to propagate radially in the space between disc and absorber. Radial arrays of microphones on the disc surface sense sound pressure amplitude and phase, from which impedance is calculated.

3 Claims, 6 Drawing Figures

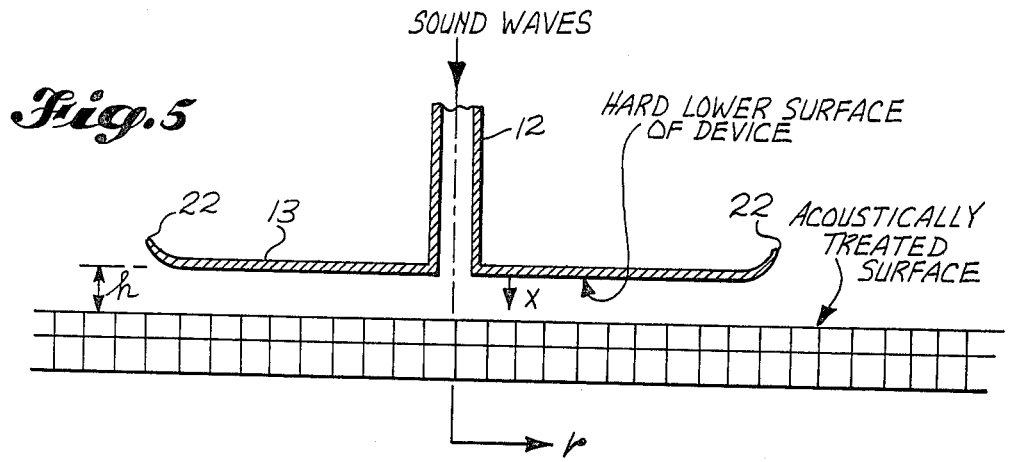
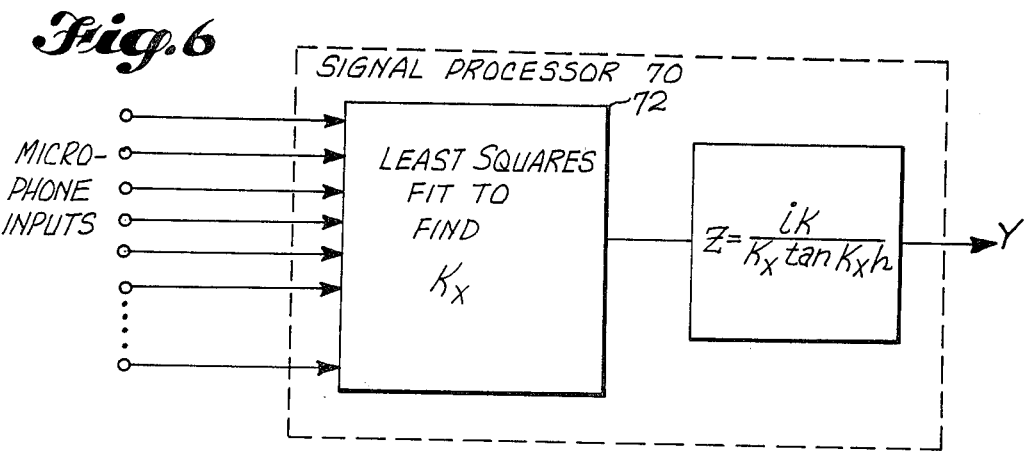

PORTABLE APPARATUS FOR MEASURING ACOUSTIC IMPEDANCE AT THE SURFACE OF CURVED SOUND ABSORBER

This invention relates to acoustic impedance measuring apparatus and more particularly to such an apparatus for determining the acoustic properties of sound absorbing linings as installed in ducts of jet engines. This apparatus is also applicable for measuring the acoustic impedance of other absorptive surfaces, including for example, acoustic wall and ceiling panels.

Heretofore, destructive testing has been used to evaluate the acoustic properties of absorbers wherein a sample has been cut and tested in an impedance tube. Such method, however, does not permit quality control of completed or installed absorber panels, which may differ greatly from the test sample. A further technique involves the use of the puck of U.S. Pat. No. 3,996,788 to Purves issued Dec. 4, 1976 and assigned to The Boeing Company which measures the resistance of the face sheet, but does not, however, provide information relating to the core or in the case of double layer absorbers, the septum. Attempts to utilize the aforementioned impedance tube in the case of installed jet engine duct linings result in acoustic leakage around the perimeter of the tube at the sample, which prevents useful results.

Representative of the patent literature in U.S. Pat. No. 3,068,370 to P. J. McInnish issued Dec. 11, 1962 which shows utilization of a flexible member to enable a sonic device to conform to a test surface. Further representative of the prior art, more particularly apparatus for analyzing complex acoustic fields within a duct is U.S. Pat. No. 4,144,768 to Anderson, et al, issued Mar. 20, 1979 and assigned to The Boeing Company.

In contrast, it is accordingly an object of the present invention to provide impedance measuring means which includes means for radial propagation of sound, a flexible sound confining skirt structure, and a measurement area sound pressure averaging arrangement.

The preceding and other objects, features, and advantages of the present invention are realized in accordance with an embodiment of the present acoustic impedance measuring system wherein a flexible skirt is provided with means for keeping a constant distance between skirt and absorber panel such as a plurality of flexible ribs which are maintained in contact with the absorber panel being tested thereby providing a number of pie shaped cavities or a plurality of pins distributed over the skirt surface, with a plurality of microphones extending through the adjoining skirt portion, a loudspeaker being attached to the flexible skirt via a connecting tube which opens centrally on the rib side of the skirt whereby all microphones of the cavity are responsive to acoustic pressure in the wave propagating over the absorber panel. A further embodiment includes microphones however, associated with gas filled cavities.

A full understanding of the invention, and of its further objects and advantages and the several unique aspects thereof, will be had from the following description when taken in conjunction with the accompanying drawings in which:

FIG. 5 is a diagram depicting parameters of the system used for determining acoustic impedance through a signal processor; and FIG. 6 is a block diagram of a signal processor used for calculating the acoustic impedance of a curved absorber from a plurality of microphone signals.

Figure 1:
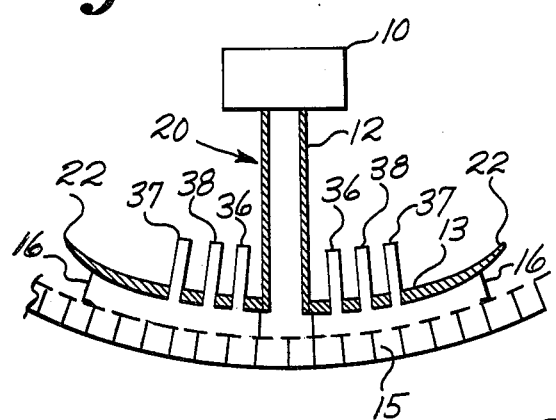
FIG. 1 is a side sectional view of a first embodiment of the present invention microphones.
Figure 2:
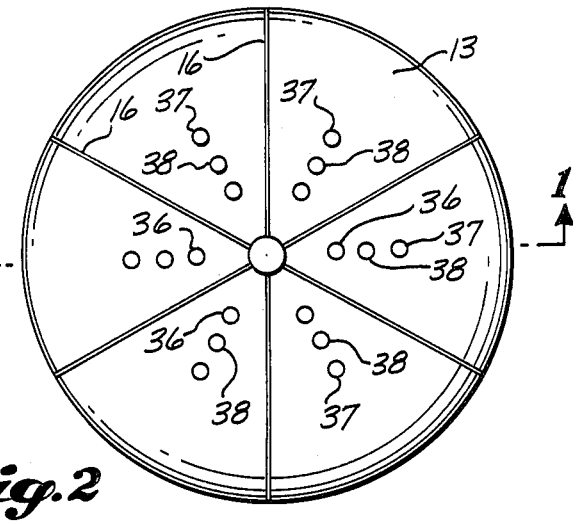
FIG. 2 is a bottom view of the flexible skirt of FIG. 1 showing flexible ribs and three or more microphones in each section between ribs.

Turning to FIG. 1 it can be seen that loudspeaker 10 is connected to one end of tube 12, the other end of tube 12 being connected to flexible skirt 13. As the impedance meter is pressed against curved absorber 15, several flexible, radially extending ribs maintain a constant channel height between skirt 13 and absorber 15. A channel height between 0.25" and 0.5" will allow measurements at frequencies up to about 8 KHz before possibility of a second acoustic mode to propagate in the channel makes data analysis more difficult and introduces the requirement for additional microphones in each radial array. This particular frequency limit is not inherent in the device, but can be changed by scaling, e.g., a reduction of the channel height by a factor of two will double limiting frequency. Ends 22 of skirt 13 are turned away from the absorber 15 to form a horn like end structure thereby reducing sound reflections. In the bottom view of FIG. 2 the arrangement of radial arrays of microphones 36, 37 and 38 in one or more of sections between ribs 16 is shown. Absorber characteristics are usually somewhat non-uniform over the surface of the panel and hence measurements from a number of microphones at the same radial location but at different circumferential locations are averaged electronically in order to yield the sought after average impedance.

Figure 3:
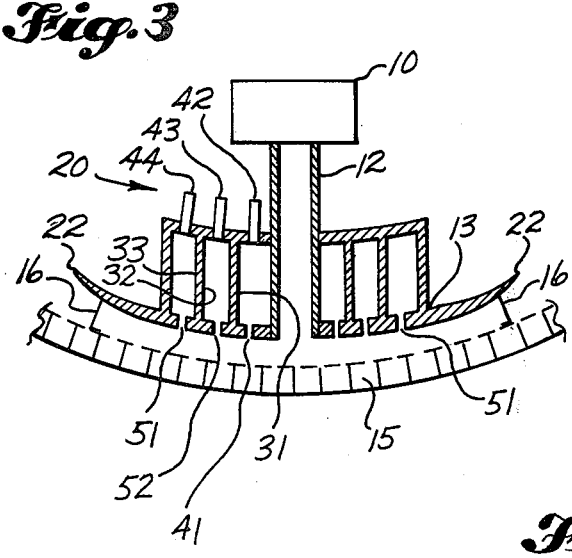
FIG. 3 is a side sectional view of a second embodiment of the present invention housing showing annular, gas-filled cavities with associated microphones.
Figure 4:
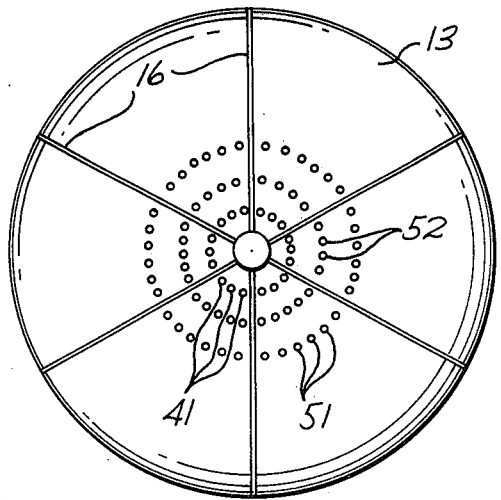
FIG. 4 is a bottom view of the flexible skirt of FIG. 3 showing flexible ribs and also small holes used to couple gas filled cavities to the channels.

In FIG. 3 of the gas filled version of the device it is seen that circumferentially extending gas filled cavities 31, 32, and 33 are connected to the channel between skirt 13 and absorber 15 by circumferential arrays of holes 41, 52, and 51. By using helium gas in cavities 31, 32, and 33 circumferential non-uniformities in the cavities have decayed before being picked up by microphones 42, 43, and 44, thereby accomplishing the desired averaging over the area of measurement.

Recognizing now from the preceding that the sound waves, which propagated from loudspeaker 10 through tube 12 are constrained to propagate radially outwards between the lower surface of flexible skirt 13 and acoustical absorber surface 15, and turning to FIG. 5 it is seen that the essential geometry of the apparatus is defined by a (r, x) cylindrical coordinate system. Stationary (or time independent) solutions of the wave equation for sound are described by the Helmholtz equation:

$$\Delta^2 p + k^2 p = 0 \tag{1}$$

where k is the wave number $=2\pi f/c=2\pi/\lambda$ and f is frequency, c is the speed of sound, $\lambda$ is wavelength and p is the acoustic pressure (the fluctauting pressure).

If the acoustic absorber is uniform, then the resulting outward propagation will have no azimuthal variation, and we need only consider solutions in the variables r and x. If the treatment is not quite uniform, then the "best fit" solution procedure described hereinafter will result in an average or "effective" impedance measurement.

In the cylindrical region outside the central core, we can write the Helmholtz equation solution with no aximuthal variation as $$p(r,x) = [Ae^{ik_x x} + Be^{-ik_x x}]\left[H_o^{(1)}\left(\sqrt{k^2 - k_x^2}\, r\right) + RH_o^{(2)}\left(\sqrt{k^2 - k_x^2}\, r\right)\right] \quad (2)$$

where:
$H_o$ are Hankel functions of 1st and 2nd kinds,
$k_x$ is a propagation constant,
A is the unkown outgoing wave amplitude, B is a constant to be determined from the boundary conditions, and R is the reflection coefficient (unknown) of the termination flare.

The hardwall boundary condition at x=0 (the surface of the device) is $$(dp/dx) = 0 \quad (3)$$

so that $ik_x A - ik_x B = 0$, i.e. $B = A$ $$p(r,x) = A \cos k_x x\, F(k_x, r) \quad (4)$$

where $F(k_x, r)$ represents the radial dependence.

The impedance boundary condition at x=h is $$(dp/dx) = ikp/Z \quad$$

where Z is the acoustic impedance of the treated surface, i.e.

$$AF(k_x,r)k_x \sin k_x h = (ik/Z)AF(k_x,r) \cos k_x h$$

So $$k_x \tan k_x h = ik/Z \quad (6)$$

Both of the microphone arrangements shown in FIGS. 1 and 3 have the same function; to determine the radial variation of the acoustic pressure (both magnitude and phase). So that, given the values of p at a set of radial locations on the hard surface, a least squares error fit can be made to $$p(r,x) = AF(k_x,r) \quad (7)$$

That is, the values of A, R and $k_x$ (all complex) are found which minimize the sum of squared errors. Once $k_x$ has been found, substitution into equation 6 gives $$Z = i(k/k_x) \cot k_x h$$

where Z is the acoustic impedance.

In signal processor 70 then of FIG. 6, microcomputer means 72 is utilized to implement the function of minimizing the sum of squared errors and providing $k_x$ which is then utilized in calculating means 74 to provide Z, the desired acoustic impedance of absorber 15.

We claim:
1. An acoustic measurement system for determining the acoustic impedance of sound absorbing panels having a curved surface area comprising:
   a flexible skirt member having a curved surface area, said flexible skirt member including a plurality of members for retaining said flexible skirt member spaced equidistantly from said sound absorbing panel;
   means coupled to the region between the curved surface area of said flexible skirt member and the curved surface area of said sound absorbing panel for providing radial propagation of sound through said region;
   a plurality of sound receiving transducers distributed over said flexible skirt member and the curved surface area of said sound absorbing panel; and,
   said processing means coupled to said plurality of said receiving transducers for providing a signal representative of the impedance of said sound absorbing panel.
2. The invention according to claim 1 wherein said region includes a plurality of pie shaped channels.
3. The invention according to claim 1 wherein said flexible skirt member includes a plurality of holes extending therethrough, said holes being coupled to a plurality of gas filled cavities.

* * * * *